(12) United States Patent
Suttin et al.

(10) Patent No.: US 10,350,036 B2
(45) Date of Patent: Jul. 16, 2019

(54) SYSTEM AND METHOD FOR IMPROVED INTRA-ORAL PROTOCOL AND CALIBRATION

(71) Applicant: Biomet 3i, LLC, Palm Beach Gardens, FL (US)

(72) Inventors: Zachary B. Suttin, West Palm Beach, FL (US); Joell Cruz, North Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 14/923,048

(22) Filed: Oct. 26, 2015

(65) Prior Publication Data

US 2016/0051346 A1 Feb. 25, 2016

Related U.S. Application Data

(63) Continuation of application No. 13/742,428, filed on Jan. 16, 2013, now Pat. No. 9,198,627.

(51) Int. Cl.
*A61C 9/00* (2006.01)
*A61B 6/14* (2006.01)
(Continued)

(52) U.S. Cl.
CPC ............ *A61C 9/0053* (2013.01); *A61B 1/045* (2013.01); *A61B 1/24* (2013.01); *A61B 6/032* (2013.01);
(Continued)

(58) Field of Classification Search
CPC ..... A61C 13/0004; A61C 1/084; A61C 9/004; A61C 7/002; A61C 8/0001; A61C 9/0053;
(Continued)

(56) References Cited

U.S. PATENT DOCUMENTS 5,927,982 A   7/1999   Kruger
6,413,085 B1  7/2002   Lee
(Continued)

FOREIGN PATENT DOCUMENTS

EP    2 233 078 A1   9/2010
JP    2009142561 A   7/2009
(Continued)

OTHER PUBLICATIONS

"A Comparative Analysis of Intraoral 3d Digital Scanners for Restorative Dentistry" Authors Silvia Logozzo, Giordano Franceschini, Ari Kilpela, PhD, Michele Caponi PhD, Lapo Governi PhD, Luciano Blois PhD; *The Internet Journal of Medical Technolog*, ISSN: 1559-4610, 2011 vol. 5, No. 1. 15 pages.
(Continued)

*Primary Examiner* — Kenny A Cese
(74) *Attorney, Agent, or Firm* — Schwegman Lundberg & Woessner, P.A.

(57) ABSTRACT

A method of providing an accurate three-dimensional scan of a dental arch area is disclosed. The arch area has two segments and a connecting area between the two segments. The connecting area has homogeneous features. A connecting-geometry tool with at least one definable feature is affixed to the arch area. The definable feature overlays at least part of the connecting area. The arch area is scanned to produce a scanned dataset of the arch area. The definable feature of the connecting-geometry tool on the connection area is determined based on the scanned dataset. The dimensions of the arch area are determined based on the data relating to the definable features from the scanned dataset.

16 Claims, 7 Drawing Sheets

Related U.S. Application Data

(60) Provisional application No. 61/624,623, filed on Apr. 16, 2012.

(51) Int. Cl.
*A61C 8/00* (2006.01)
*A61B 6/00* (2006.01)
*A61B 1/045* (2006.01)
*A61B 1/24* (2006.01)
*A61B 6/03* (2006.01)
*A61B 19/00* (2006.01)

(52) U.S. Cl.
CPC .............. *A61B 6/14* (2013.01); *A61B 6/145* (2013.01); *A61B 6/586* (2013.01); *A61C 8/0001* (2013.01); *A61B 2019/5287* (2013.01); *A61B 2576/00* (2013.01)

(58) Field of Classification Search
CPC ......... A61C 7/00; A61C 8/0048; A61C 8/005; A61C 8/0089; A61C 9/0006; A61C 13/225; A61C 8/0096; A61C 11/00; A61C 13/0003; A61C 8/0034; G06F 17/50; G06K 9/46; A61B 6/145; A61B 6/586; A61B 1/045; A61B 1/24; A61B 6/032; A61B 6/14
See application file for complete search history.

(56) References Cited

U.S. PATENT DOCUMENTS

| | | | |
|---|---|---|---|
| 7,286,954 B2 | 10/2007 | Kopelman | |
| 7,890,290 B2 | 2/2011 | Kopelman | |
| 8,021,150 B2 | 9/2011 | Fuentevilla | |
| 9,198,627 B2 | 12/2015 | Suttin et al. | |
| 2006/0251220 A1 | 11/2006 | Young et al. | |
| 2006/0257817 A1* | 11/2006 | Shelton | A61C 1/084 433/75 |
| 2008/0153067 A1 | 6/2008 | Berckmans et al. | |
| 2008/0292779 A1 | 11/2008 | Mercuri et al. | |
| 2009/0162813 A1* | 6/2009 | Glor | A61C 1/084 433/196 |
| 2009/0176182 A1* | 7/2009 | Carrillo Fuentevilla | A61C 1/084 433/9 |
| 2009/0248184 A1 | 10/2009 | Steingart | |
| 2010/0268071 A1 | 10/2010 | Kim | |
| 2011/0008751 A1* | 1/2011 | Pettersson | A61C 1/084 433/167 |
| 2011/0275029 A1 | 11/2011 | Gao | |
| 2012/0072178 A1* | 3/2012 | Beaudry | A61C 8/0077 703/1 |
| 2012/0088208 A1* | 4/2012 | Schulter | A61C 8/0001 433/173 |
| 2013/0017507 A1* | 1/2013 | Moffson | A61C 1/084 433/27 |
| 2013/0273492 A1 | 10/2013 | Suttin et al. | |
| 2014/0051037 A1* | 2/2014 | Fisker | A61C 8/0048 433/213 |

FOREIGN PATENT DOCUMENTS

| | | |
|---|---|---|
| JP | 2011509812 A | 3/2011 |
| JP | 2012515026 A | 7/2012 |
| JP | 2015516856 A | 6/2015 |
| WO | WO 2007/005490 | 1/2007 |
| WO | WO 2008/051129 | 5/2008 |
| WO | WO-2009119620 A1 | 10/2009 |

OTHER PUBLICATIONS

"Application of Intra-Oral Dental Scanners in the Digital Workflow of Implantology," Authors Wicher J. van der Meer, Frank S. Andriessen, Daniel Wismeijer, Yijin Ren. *PLOS One*, 2012. 8 Pages.
International Search Report, PCT/US2013/035923, dated Jul. 25, 2013, 7 pages.
Written Opinion of the International Searching Authority, PCT/US2013/035923, dated Jul. 25, 2013.
"U.S. Appl. No. 13/742,428, Final Office Action dated May 19, 2015", 17 pgs.
"U.S. Appl. No. 13/742,428, Non Final Office Action dated Dec. 2, 2014", 13 pgs.
"U.S. Appl. No. 13/742,428, Notice of Allowance dated Sep. 16, 2015", 14 pgs.
"U.S. Appl. No. 13/742,428, Response filed Mar. 2, 2015 to Non Final Office Action dated Dec. 2, 2014", 8 pgs.
"U.S. Appl. No. 13/742,428, Response filed Aug. 11, 2015 to Final Office Action dated May 19, 2015", 8 pgs.
"U.S. Appl. No. 13/742,428, Response filed Nov. 4, 2014 to Restriction Requirement dated Sep. 16, 2014", 7 pgs.
"U.S. Appl. No. 13/742,428, Restriction Requirement dated Sep. 16, 2014", 7 pgs.
"European Application Serial No. 13717940.4, Response filed Jul. 30, 2015 to Communication pursuant to Rules 161(1) and 162 EPC dated Jan. 21, 2015", 12 pgs.
"Japanese Application Serial No. 2015-507050, Office Action dated Aug. 2, 2016", (W/ English Translation), 9 pgs.
"Japanese Application Serial No. 2015-507050, Office Action dated May 9, 2017", With English Translation, 13 pgs.
"Australian Application Serial No. 2013249682, First Examiners Report dated Jul. 24, 2017", 3 pgs.
"Japanese Application Serial No. 2015-507050, Response filed Jul. 31, 2017 to Office Action dated May 9, 2017", (W/ English Translation), 11 pgs.
"Australian Application Serial No. 2013249682, Response filed Jun. 26, 2018 to First Examiners Report dated Jul. 24, 2017", 45 pgs.
"European Application Serial No. 13717940.4, Response filed Nov. 13, 2017 to Office Action dated Feb. 1, 2017", 11 pgs.
"Japanese Application Serial No. 2015-507050, Examiners Decision of Final Refusal dated Jan. 23, 2018", (W/ English Translation), 6 pgs.
"Japanese Application Serial No. 2015-507050, Response filed May 21, 2018 to Examiners Decision of Final Refusal dated Jan. 23, 2018", (W/ English Translated Claims), 17 pgs.
"Canadian Application Serial No. 2,869,222, Office Action dated Oct. 29, 2018", 4 pgs.

* cited by examiner

FIG. 2A  FIG. 2B

SYSTEM AND METHOD FOR IMPROVED INTRA-ORAL PROTOCOL AND CALIBRATION

TECHNICAL FIELD

This disclosure relates to dental restoration techniques and specifically for obtaining accurate intra-oral scan results for the connecting areas between segments of an arch.

BACKGROUND

Restorations in the form of dental prosthetics may be necessary to address partially or wholly edentulous conditions. Traditionally, such restorations have been performed by forming a model by providing an impression of the affected areas of a patient's mouth, developing a stone model from the impression, and fabricating a customized prosthetic device on the stone model. The process is cumbersome and requires excessive intrusion into the patient's mouth. However, the stone model provides enough accuracy to produce prosthetics that minimize stress and interference with the edentulous area.

Recently, intra-oral scanning (IOS) has emerged as a preferred dental impression technique for conventional (tooth-borne) and implant dentistry. IOS typically involves using a handheld scanner having optical sensors to capture a three-dimensional dataset of the area of interest. The resulting dataset may be used for constructing a model for preparing patient specific prosthetics. An example of using such datasets to construct a model may be found in U.S. Patent Publication No. 2011-0183289, filed on Dec. 7, 2007, titled "Method For Manufacturing Dental Implant Components." The IOS process offers a very efficient and cost-effective means by which to acquire and transmit anatomic data for purposes of forming a prosthetic. While the accuracy of IOS has been proven to be sufficient for single tooth restorations and short-span multiple tooth segments, it is often contraindicated for scanning larger edentulous segments such as a full arch area scan or potentially smaller segments which are "highly" edentulous.

There are many potential contributing factors for the difficulty of applying IOS to full arch restorations. For example, small adjacent site-to-site errors, while having minimal impact on single tooth or short-span multiple tooth segments, may accumulate where the resulting error throughout the full arch is unacceptable.

While IOS is robust when scanning well defined landmarks (i.e., teeth vs. tissue), large homogeneous areas needed for full arch restoration are problematic. As an arch is scanned, if there are homogeneous segments, especially large ones, these landmarks are vague and, therefore, cannot be interpreted as accurately. The teeth serve as robust landmarks in a scan of an arch, but soft-tissue surfaces between segments of the arch such as the mouth surfaces and the tongue are homogenous surfaces and are therefore difficult to scan accurately. The connecting area(s) such as the tongue or the roof of the mouth are essentially seen as "oceans" of homogeneous surfaces in the scan dataset in that these homogeneous surfaces are difficult to distinguish from each other because they all appear the same in the scanned dataset.

The geometry acquired for the cross-arch connecting geometry (i.e., the tongue or the palate) covers a relatively large area, but only a small portion of the data within this area is scanned. This may lead to cross-arch error and/or full arch distortion and is often most visible when assessing the posterior segments of the resulting model, as these zones are adjacent to the greatest area of "digital dead space" (or the space not scanned). For example, FIG. 1A shows a full arch area 100 which includes an arch 102 having a number of teeth 104 on two segments 106 and 108. In this example, edentulous areas between the teeth 104 on the arch 102 require the application of a dental restoration process. A cross-arch geometric connecting area 110 separates the two segments 106 and 108 of the arch 102. In order to form proper restorative devices, such as a bridge for the arch 102 the distance between the two segments 106 and 108 must be accurately determined.

Scanning the connecting area 110 has limited effectiveness in determining accurate dimensions because the connecting area 110 does not have any distinct features. The connecting geometry area 110 is relatively non-defined (or vague). While a scan of this area eliminates the digital dead space, the quality of the data does not provide for a sufficiently precise digital acquisition and subsequent reconstruction of the dental anatomy of the arch area 100. Such errors are magnified at the end of the segments 106 and 108 due to the geometry of the segments 106 and 108 in relation to the front of the arch 102. For example, a cumulative error of over 180µ for this posterior cross-arch span connecting area 110 shown in FIG. 1A in a resulting model would be much greater than the tolerance allowed to passively seat a full-arch denture supporting bar framework. While the distortion may be small, the clinical relevance of this error is significant, preventing the proper fabrication of the restorative device.

FIG. 1B shows a full arch area 150 which includes an arch 152 with a full edentulous condition with two segments 156 and 158. In this example, edentulous areas on the arch 152 require the application of a dental restoration process. In this example, a series of implants have already been implanted in the arch 102 in preparation for modeling of the arch area 150. Each of the implants 170 has a gingival healing abutment 170 that extends through the soft tissue. A cross-arch geometric connecting area 160 separates the two segments 156 and 158 of the arch 152. In order to form proper restorative devices, such as a bridge for the arch 152 the distance between and around the two segments 156 and 158 must be accurately determined.

FIG. 2A shows a control model 202 formed by a 3Shape laser scan of a cast of the arch area 150 and implants 170 shown in FIG. 1B. The control model 202 is very accurate since it is prepared by scanning the cast produced from a mold taken from the area of interest. Such a larger scan system is more accurate than the handheld scanners used for the IOS techniques because of the differences in the associated algorithms required for acquiring the data and reconstructing the 3-dimensional datasets. FIG. 2B shows a model 204 that is manufactured using a scan dataset from the arch area 150 taken by known IOS techniques. As explained above, the homogeneity of the connecting area 160 results in dimensional inconsistencies between the model 204 and the actual arch area 150. FIG. 2C shows the scan model 204 in FIG. 2B overlaying the control model 202 in FIG. 2A. As shown in FIG. 2C, shaded areas 210 represent distortions between the actual dimensions of the arch area 150 represented by the control model 202 produced by casting and the model 204 produced by known intra-oral scanning techniques. As shown in FIG. 2C, the distortions 210 occur throughout the entire arch, but are greatest on the ends of the segments of the model 204 because of the inaccuracies in determining the dimensions of the connecting geometry between and around the segments. Such inaccuracies may result in positive stretching where the segments of the model are wider than those of the actual arch area. The positive stretching may be seen by the arrows labeled by "EE" in FIG. 2C. The inaccuracies may also result in a model which suffers from negative stretching where the segments are narrower than the actual arch areas. The resulting models therefore are not useful in the restorative process since the resulting prosthesis devices will not interface correctly with the actual arch area.

One proposed solution has been to spray the connecting geometry area with a coating in order to help establish scannable features within the connecting area. The arch and the connecting area are then scanned and a resultant dataset is produced. However, the spraying technique still results in inaccurate scans because the features of the connecting area such as the tongue, assuming that they contain geometry which is distinguishable enough to provide robust data, may move from the location captured during the scan.

Thus, a need exists to improve the accuracy of known intra-oral scanning to enable reliable full arch scanning There is a need to calibrate an intra-oral scan dataset with known dimensions to improve the accuracy of the scanned dataset. There is a further need to perform real-time error correction on a scan dataset in the process of acquisition of the scanned data points.

SUMMARY

An example of the present disclosure is a method of providing a three-dimensional scan of a dental arch area, the arch area having two segments and a connecting area between the two segments. A connecting-geometry tool with at least one definable feature is affixed relative to the dental arch area. The at least one definable feature overlays at least part of the connecting area. The arch area is scanned to produce a scanned dataset of the arch area. Data relating to the definable feature of the connecting-geometry tool overlaying the connecting area is determined based on the scanned dataset. The dimensions of the connecting area are determined based on the data relating to the definable feature.

Another example is a system for producing a scanned dataset of a dental arch area, the dental arch area including two segments and a connecting area between the two segments. The system includes a controller and an intra-oral scanner coupled to the controller. A connecting-geometry tool affixable to the dental arch area overlays the connecting area. The connecting-geometry tool includes at least one definable feature. The controller is operative to accept scan data from the intra-oral scanner and determine the dimensions of the connecting area based on data relating to the definable feature.

Another example is a method of producing a scanned dataset of a dental arch area, the arch area including two segments separated by a connecting area. A computed tomography scan is performed over the arch area. The computed tomography scan includes at least one landmark object in the arch area. A reference dimension value of the landmark object is determined in the arch area from the computer tomography scan. An intra-oral scan is performed over the arch area including the at least one landmark object and the connecting area. A dimension of the landmark object in the arch area is determined from the intra-oral scan. The reference dimension value is compared with the dimension of the landmark object determined from the intra-oral scan to determine error correction information. The error correction information is applied to the intra-oral scan dataset of the arch area to produce a corrected intra-oral scan dataset.

Another example is a method of providing a three-dimensional scan of a dental arch area. The arch area has two segments and a connecting area between the two segments. The arch area includes a first implant embedded in the arch area. The first implant has a central axis. A connecting-geometry tool with at least one definable feature is coupled to the first implant. The at least one definable feature is transverse to the central axis of the implant. The at least one definable feature overlays at least part of the connecting area. The arch area is scanned to produce a scanned dataset of the arch area. Data relating to the definable feature of the connecting-geometry tool overlaying the connecting area is determined based on the scanned dataset. The dimensions of the connecting area are determined based on the data relating to the definable feature.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 2A is a top view of a control model formed by a scan of a casting of the arch area shown in FIG. 1B;

FIG. 2B is a top view of a flawed model formed from a direct scan of the arch area shown in FIG. 1B using known intra-oral scan techniques;

Figure 1A:
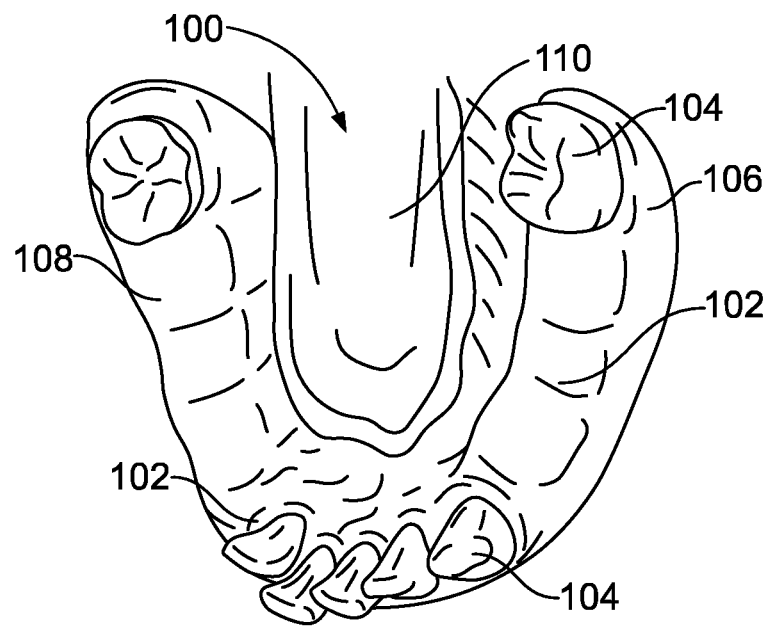
FIG. 1A is a top view of an dental arch area of a patient with partial edentulous areas requiring restoration.
Figure 1B:
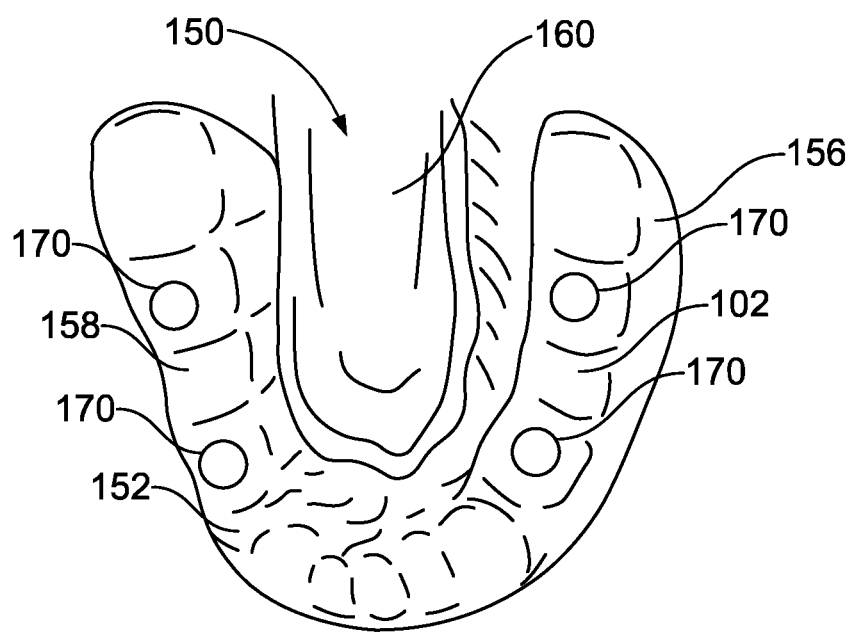
FIG. 1B is a top view of another dental arch area of a patient with entire edentulous areas requiring restoration.
Figure 2C:
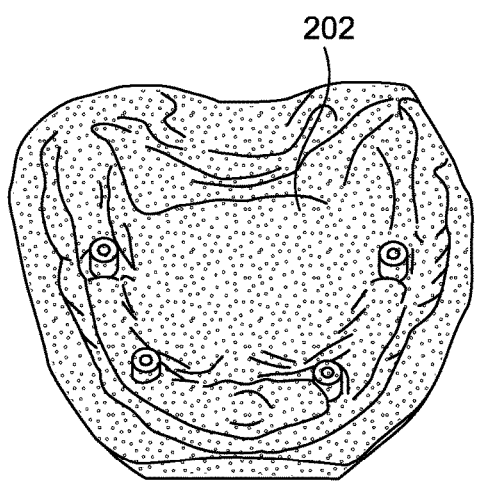
FIG. 2C is a top view of the model shown in FIG. 2B interposed on the control model in FIG. 2A to show the misalignment due to scanning error.
Figure 2C:
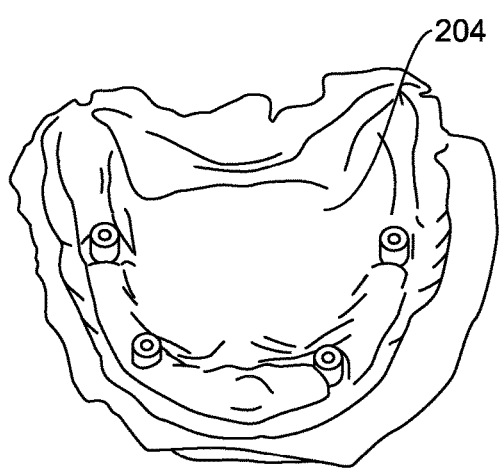
Figure 2C:
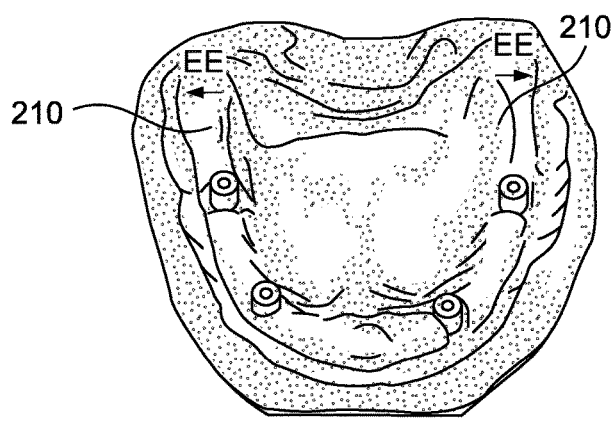

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Figure 3A:
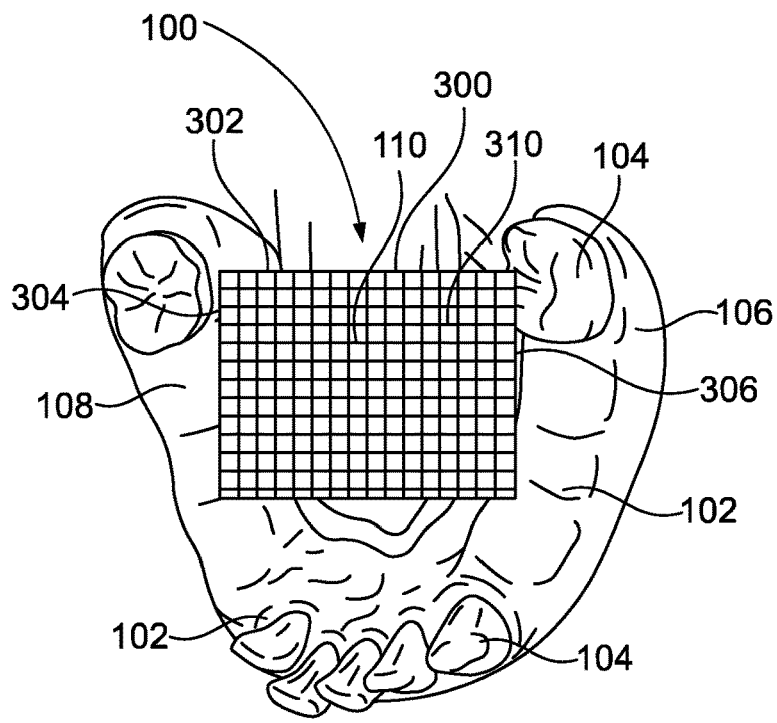
FIG. 3A is a top view of a homogeneous mesh grid affixed to the arch area shown in FIG. 1A prior to intra-oral scanning.

FIG. 3A is a top view of the arch area 100 shown in FIG. 1A with an affixed connecting-geometry tool 300 to improve the accuracy of a full arch area intra-oral scan. The arch area 100 includes the arch 102 which includes teeth 104 and edentulous areas requiring restoration. The connecting area 110 is disposed between the segments 106 and 108 which form the arch 102. As is known, a restorative process may involve the creation of a model of the arch area 100 which may then be used for fabrication of restorative devices such as a dental bridge matching the features of the arch area 100. The exemplary dental bridge would be supported by restorative components, such as implants and abutments that may be inserted in the edentulous areas of the arch 102. Of course, restorative processes may address smaller segments of the arch such as partial segments with more high edentulous areas.

The model of the dental arch area 100 may be created by the use of a dataset obtained from three-dimensional intra-oral scanning One example of intra-oral scanning involves a handheld three-dimensional intra-oral scanner that may be used to scan the arch area 100 to produce the dataset. An example three-dimensional intra-oral scanner may include two stereo cameras that capture image data from an area of interest such as an individual tooth or the entire arch area 100. Exemplary intra-oral scanner systems may include but not be limited to the 3M Lava C.O.S., the Cadent iTero digital impression system, and the Sirona CEREC intraoral scanner. Corresponding software captures all images from the scanner in real-time, generates a three-dimensional model of the area of interest, and sends the dataset to a computer. Using software on the computer, the resulting dataset may be used to fabricate models of the arch area 100 for preparation of restoration devices. Since the dimensions of the arch area 100 are necessary to produce a model for the entire arch area 100, the scanned dataset includes images of the connecting area 110.

During the scan, the digital dead space represented by the connecting area 110 may be covered with a "connecting-geometry" tool having scannable or definable features to bridge the gap between the open segments 106 and 108 of the arch 102. The connecting-geometry tool is temporarily affixed to the area of interest such as the arch 102 and extends over the connecting area 110. The connecting-geometry tool ideally contains distinct features that register in the scan dataset produced when scanning the connecting area 110. The resulting scanned dataset therefore includes more accurate scans of both the arch 102 and the connecting area 110 with the connecting-geometry tool because of the inclusion of scannable or definable features overlaying the connecting area 110.

One example of a connecting-geometry tool is a homogeneous mesh grid 300 shown in FIG. 3A. The mesh grid 300 is anchored on one or both of the segments 106 and 108 of the arch 102 prior to scanning the arch area 100. This may be done by an adhesive such as a dental acrylic applied to the segments 106 and 108 and the mesh grid 300 or by a mechanical device such as a pin or pins attaching the segments 106 and 108 to the mesh grid 300. Alternatively, if implants are present in the arch 102, the mesh grid 300 may be coupled to those implants, either directly or indirectly, through components such as healing abutments attached to the implants as will be explained below. The mesh grid 300 in this example is fabricated using metal and includes a frame 302 having two side rails 304 and 306. As explained above, the side rails 304 and 306 are preferably affixed to the segments 106 and 108 during the scanning procedure. The mesh grid 300 includes uniform squares 310 which are of a set dimension. The dimensions of the squares 310 are selected based on scanner resolution to define the connecting geometry area 110 and in this example are 2 mm square. Of course other materials such as polymers may be used for the mesh 300. Further, other dimensions may be selected for the size of the squares 310. Finally, other shapes such as triangles, polygons, etc. may be used instead of the squares 310.

With the mesh grid 300 affixed to the arch 102, a scan may be taken of the arch 102 and the connecting geometry area 110. The features of the arch area 100 such as the teeth 104 provide distinct features and, thus, accurate dimensions may be obtained by the resulting scan dataset of the arch 102. Since the mesh grid 300 overlays the connecting geometry area 110, the separation between the segments 106 and 108 is also well defined and the scan of the connecting geometry area 110 discerns distinct features of the grid 300. Data relating to the definable features of the connecting-geometry tool such as the mesh grid 300 on the connecting area 110 is determined based on the scanned dataset. The dimensions of the connecting area 110 are determined based on the data relating to the definable features and thereby provides accurate dimensions of the connecting geometry area 110. The resulting dataset may be used to create an accurate model of the arch 102 and the connecting geometry area 110 for implant installation and/or restoration processes.

Figure 3B:
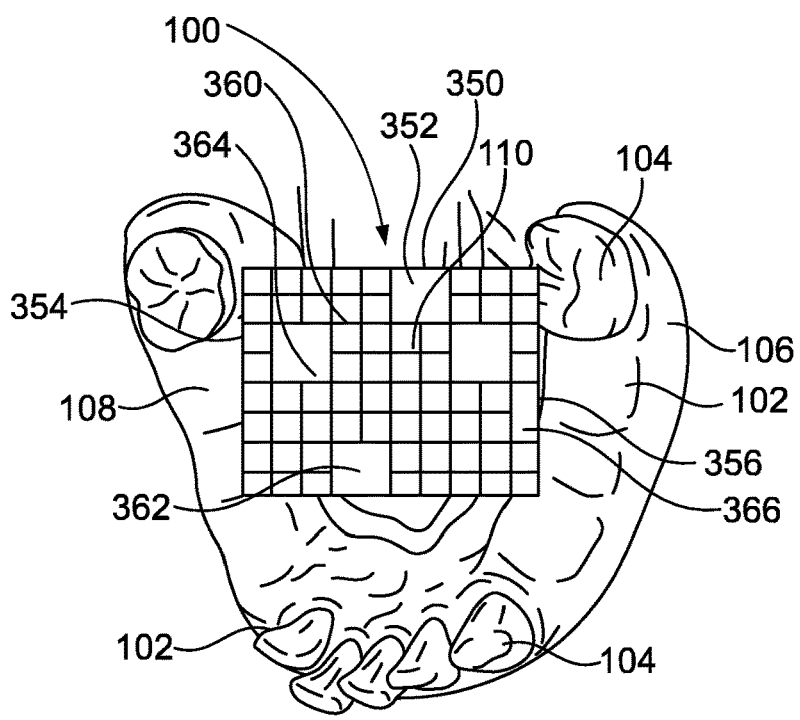
FIG. 3B a top view of a heterogeneous mesh grid affixed to the arch area in FIG. 1A prior to intra-oral scanning.

FIG. 3B shows another type of a connecting-geometry tool which is a heterogeneous mesh grid 350 that is affixed to the arch 102 in FIG. 1A prior to scanning the arch area 100. The mesh grid 350 in FIG. 3B contains heterogeneous features of known dimensions and distances to provide recognition in the scanned dataset and provide dimensional data for error assessment. The mesh grid 350 in this example is fabricated in wire and includes a frame 352 having two side rails 354 and 356. The mesh grid 350 includes a grid structure 360 with a number of shapes in the grid structure 360 such as a first square 362, a second square 364 and a rectangle 366. In this example, the square 362 has a dimension of 4×4 mm, the square 364 has a dimension of 1.5×1.5 mm and the rectangle 366 has a dimension of 1×2 mm. The distances between the shapes 362, 364 and 366 are also selected to assist in the analysis of the scan dataset. The heterogeneous grid shapes of the mesh grid 350 provide better references because of the distinct nature of each of the grid shapes and the known dimensions between them. The use of the known dimensions of the shapes in the grid structure 360 may be compared with the dimensions obtained from the scan dataset of these shapes and an error correction factor may be determined based on the difference of the scanned dimensions and the known actual dimensions. The scanned dataset may therefore be corrected based on the error correction factor to produce a corrected intra-oral scan dataset.

Figure 4:
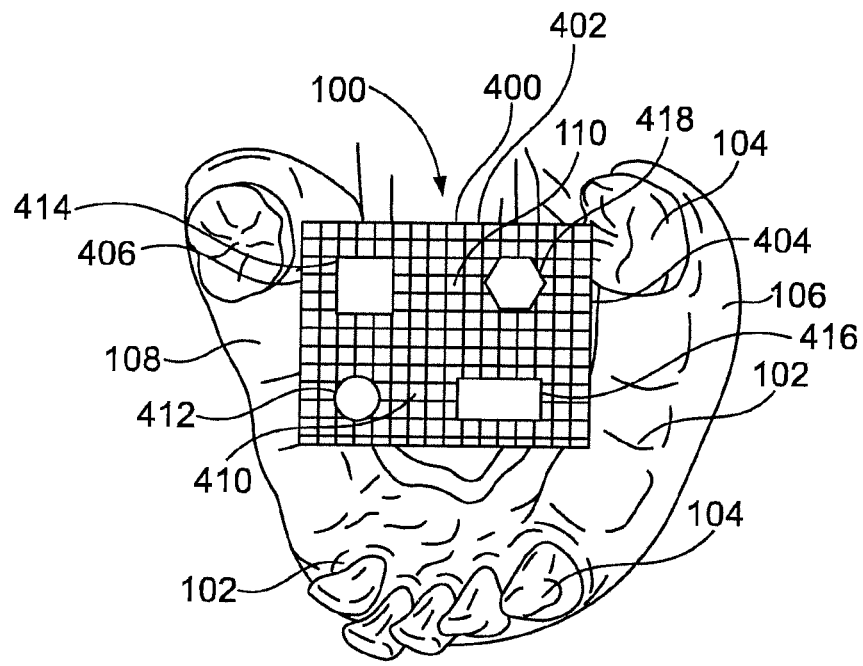
FIG. 4 is a top view of a mesh grid affixed to the arch area in FIG. 1A prior to intra-oral scanning, where the mesh grid includes objects having different geometric dimensions overlaying the connecting area.

FIG. 4 shows another type of a connecting-geometry tool to improve the accuracy of full arch scans. The connecting-geometry tool in FIG. 4 is a mesh grid 400 that may be inserted in the arch area 100 in FIG. 1A. The mesh grid 400 in this example is fabricated in metal and includes a frame 402 having two side rails 404 and 406. As explained above, the mesh arch 400 is affixed to the arch 102. The mesh 400 includes uniform squares 410 which are of a set dimension and are composed in a grid. The uniform squares 410 provide distinguishable features when overlaying the connecting geometry area 110. Further features are attached to points in the grid and may include objects 412, 414, 416 and 418 that are included to provide distinct dimensional features to the mesh grid 400. The objects can include a cylindrical shape such as object 412, a square shape such as object 414, a rectangular shape such as object 416 and a hexagonal shape such as object 418. The objects 412, 414, 416 and 418 form a library of features with known dimensions for reference to the features obtained from the scanned dataset.

In FIG. 4, the mesh 400 includes objects such as the objects 412, 414, 416 and 418 of known dimensions (and preferably with known distances relative to each other). The mesh 400 is overlaid on the connecting geometry area 110 in the arch area 100. The mesh 400 and objects 412, 414, 416 and 418 create identifiable features overlaying the connecting geometry area 110. The known dimensions may include the diameter of the circle object 412, the length and width of the square and rectangle objects 414 and 416, and the side lengths and height of the hexagon object 418. These objects and their dimensions, once scanned, are automatically identified by software algorithms used to analyze the scanned dataset. An error (or distortion) assessment may then be executed to determine the skew in the scan data by assessing the intra-oral scan interpretation of the known dimensions of the objects in comparison with the actual dimensions of the objects. The output of this error assessment allows for correction of the entire scan dataset (including features of the arch area 100 and connecting geometry area 110). This technique is analogous to scanning both the patient and a calibration object simultaneously, and then error correcting the scan dataset based on the interpretation of the dimensions determined from the scan of the calibration object(s).

An improved error correction process may be employed with the inclusion of objects with known dimensions in the connecting geometry area 110 such as the objects 412, 414, 416 and 418. Since the dimensions of the objects 412, 414, 416 and 418 on the mesh 400 are known, the scanned dimensions of such objects may be analyzed in real-time during the scan for purposes of correcting any error between the scanned dimensions of all the objects scanned in the arch area 100 and the actual dimensions of the scanned objects. The correction for any deviation may be input into the resulting subsequent data from the scanner output to correct data from the scans of the other features of the arch area 100. Such error correction may be performed in real-time as the scan data is being captured and is feasible so long as a portion of the connecting area 110 with a corresponding object of known dimensions such as any or all of the objects 412, 414, 416 and 418, is in view of the scanner throughout the scan acquisition procedure.

Another process to increase accuracy is the incorporation of data from a prior computed tomography (CT) scan of the patient in the intra-oral scanning procedure. Such CT scans are based on x-ray technology and may be made for any purpose such as for surgical planning The CT scan of the arch area 110 will capture landmark objects such as the bone and teeth in the arch area 100 but no soft tissue due to the nature of the CT scanning process. A subsequent intra-oral scan will pick up the teeth and tissue in arch area 100 but is subject to distortion in the homogeneous connecting area 110 as explained above. However, the results of the CT scan may be analyzed and compared to the dataset from the intra-oral scan to error correct the intra-oral scan dataset.

In this instance, the full arch intra-oral scan may be corrected by virtually realigning the teeth 104 (or other robust geometry) in this secondary scan to match the more accurate initial CT scan. This removes the skew in the full arch intra-oral scan without having to scan the arch area 100 with a connecting-geometry tool overlaying the connecting area 110. Providing certain landmark objects are common to both scans such as the teeth 104 in FIG. 1A, the error correction may be made to the intra-oral scan dataset based on the comparison of the reference dimensions of the landmark objects obtained from the CT scan and the dimensions obtained from the intra-oral scan of the landmark objects. The resulting error correction may be applied to the intra-oral scan dataset of the arch area to produce a corrected intra-oral scan dataset. Although preferred, not all teeth or other geometries need to be present in both scans to provide sufficient error correction.

Figure 5A:
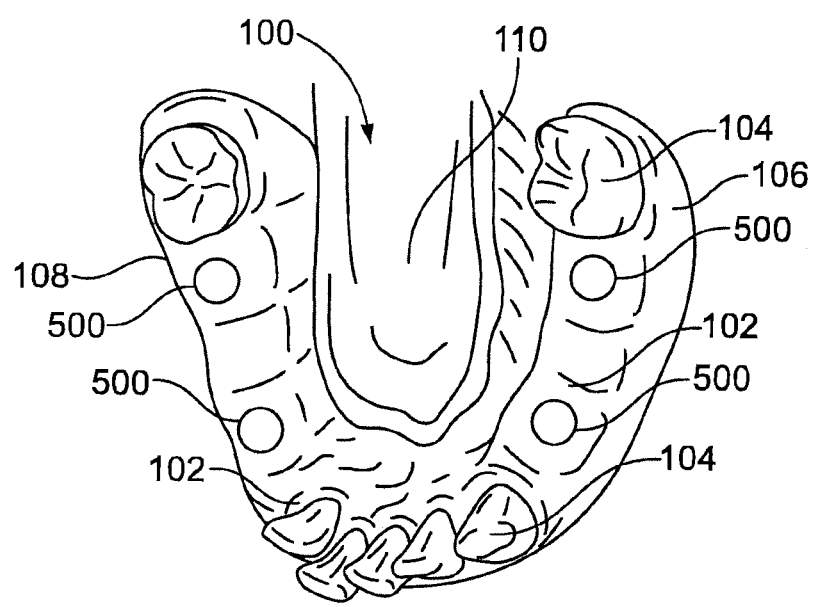
FIG. 5A is a top view of the arch area in FIG. 1A with encoded healing abutments embedded in the arch.

Specialized abutments may also be used with another type of connecting-geometry tool to increase the accuracy of the scanned dataset. FIG. 5A shows the arch area 100 in FIG. 1A where healing abutments 500 have been attached to implants (not shown) sunk into the jaw of the arch 102 for purposes of preparing the arch 102 for permanent restoration. As is known, the healing abutments 500 provide a known geometry for the gingiva above the implant. In this example, the healing abutments 500 are coded healing abutments that include information about the dimensions and locations of the abutments and underlying implants as shown in U.S. Pat. No. 6,790,040, titled "Healing components for use in taking impressions and methods for making the same," hereby incorporated by reference.

Figure 5B:
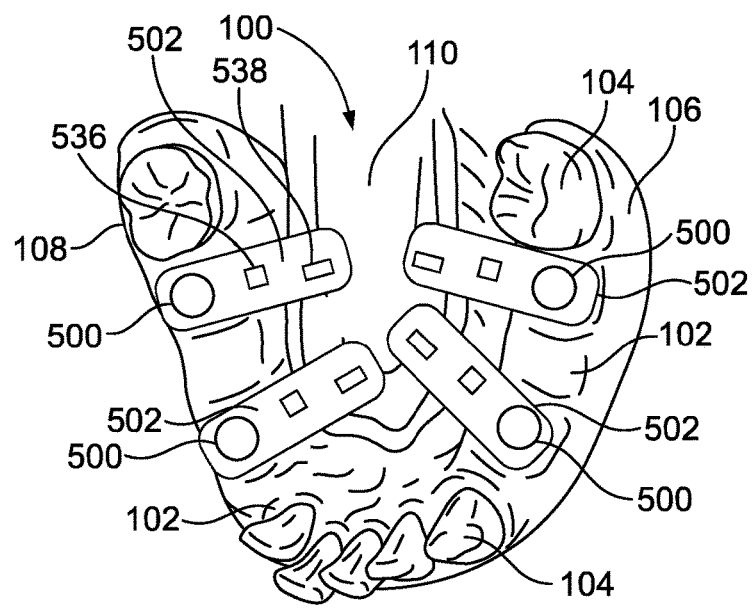
FIG. 5B is a top view of the arch area in FIG. 1A with scan plates attached to the healing abutments in FIG. 5B prior to intra-oral scanning.

FIG. 5B shows specialized scan plates 502 that are attached to the healing abutments 500 prior to scanning the arch area 100. The scan plates 502 may be extended into the connecting geometry area 110 and be used as a connecting-geometry tool on the arch area 100 in FIG. 1A. Since the scan plates 502 have distinct features, the scan dataset of the connecting area 110 provides more accurate geometrical dimensions.

Figure 5C:
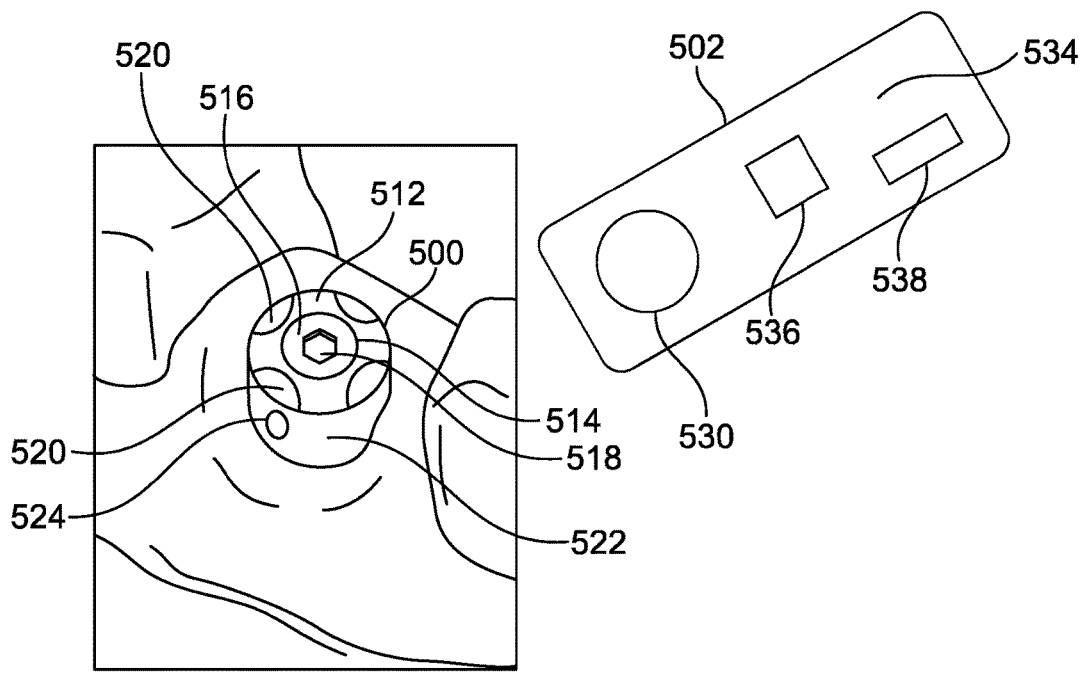
FIG. 5C is a close-up perspective view of the healing abutment and the scan plate shown in FIG. 5B.

FIG. 5C is a close-up view of a healing abutment 500 and a scan plate 502 in FIG. 5B. The healing abutment 500 includes a top surface 512 that includes a socket 514 that holds a screw (partially shown) with a screw head 516. The screw head 516 includes a socket 518 having interlocking side surfaces for the attachment of a driving device to tighten the screw to hold the abutment 500 in the implant embedded in the arch 102. The top surface 512 of the healing abutment 500 includes one or more coded features 520 that indicate known dimensional measurements and location of the healing abutment 500 and the underlying implant.

A sidewall 522 extends from the abutment 500 and includes a dimple feature 524 that serves to support and orient the scan plate 502. The scan plate 502 includes a hole 530 that is the same diameter as the abutment 500. The scan plate 502 is connected to the abutment 500 via the sidewall 522 and rests on the dimple 524 thereby fixing the scan plate 502 in place relative to the connecting area 110. Alternatively, the hole 530 may include a detent that matches the dimple 524 to assist in fixing the scan plate 502 in place. Alternatively, the scan plates 502 may include a mating post in place of the hole 530. The mating post may be locked into the socket 518 in the screw head 516 to provide a snap-in attachment of the scan plate 502. There are other ways to connect the connecting-geometry tool to the healing abutment 500.

The scan plate 502 includes a top surface 534 that has protruding objects 536 and 538 of known dimensions. Since the scan plates 502 extend into the connecting geometry area 110, the intra-oral scan may be made to detect the distinct features of the scan plates 502 such as the objects 536 and 538 or the general shape of the scan plate 502, itself. Alternatively, the portion of the scan plate may be supports for mesh structures to be extended into the connecting geometry area 110.

A clinician attaches the scan plates 502 to the healing abutments 500 in the arch area 100 prior to scan process. The scan plates 502 do not have to fill the entire connecting geometry area 110, but for optimal scanning portions of at least two scan plates 502 should be captured within each IOS digital scan frame. The scanning process of the arch 102 and the connecting area 110 with the overlaying scan plates 502 may then be commenced. As explained above, since the dimensions of the objects 536 and 538 on the scan plates 502 are known, error correction may be performed in real-time by comparing the known dimensions with those dimensions obtained when the objects are determined from the scanned dataset. The resulting scanned dataset may be error corrected in real-time.

If the scan plates 502 block underlying geometry in the arch area 100 needed to be acquired, such as the teeth 104 or other areas of interest of the arch 102, an initial scan may be taken of the arch area 100 without the scan plates 502. A second scan may then be taken of the arch area 100 with the scan plates 502 in place. The initial scan without the scan plates 502 may then be error corrected using the healing abutments 500 from the second scan as a reference object.

Other compatible devices may be incorporated with implants that are embedded in the arch 102. For example, rather than using the healing abutments 500 and plates 502 in FIG. 5B, a connecting-geometry tool may be directly coupled to the implant during the scan process and prior to the attachment of abutments. The implant has a central axis that is perpendicular to the surface of the arch 102. A connecting-geometry tool mateable to an implant has a support body that is connectable to the implant. For example, if the implant has a threaded socket, the support body of the connecting-geometry tool may be threaded. Other alternatives may include a matching member to the shape of the socket or a hexagonal connecting interface. The connecting-geometry tool mateable to an implant may include an arm that is transverse to the central axis of the implant. When the connecting-geometry tool is inserted in the implant, the arm is thereby extended over the connecting area similar to the scan plates 502 shown in FIG. 5B. As explained above, the arm provides a feature that when overlaying the connecting area 110 provides more accurate scanning Of course, any number of connecting-geometry tools mateable to an implant may be attached to implants to provide scannable features overlaying the connecting area 110 in FIG. 1A. For example, if the implants are embedded in the segments 106 and 108, the corresponding connecting-geometry tools would extend from opposite sides of the arch 102 into the connecting area 110. In short, the connecting-geometry tool may have features above the implant (like the markings from U.S. Pat. No. 6,790,040) that permit the location and orientation of the underlying implant to be discerned, while also having laterally extending portions (mesh, arms, etc.) that connect over the soft tissue of connecting area 110 such as the tongue or palate.

Figure 6A:
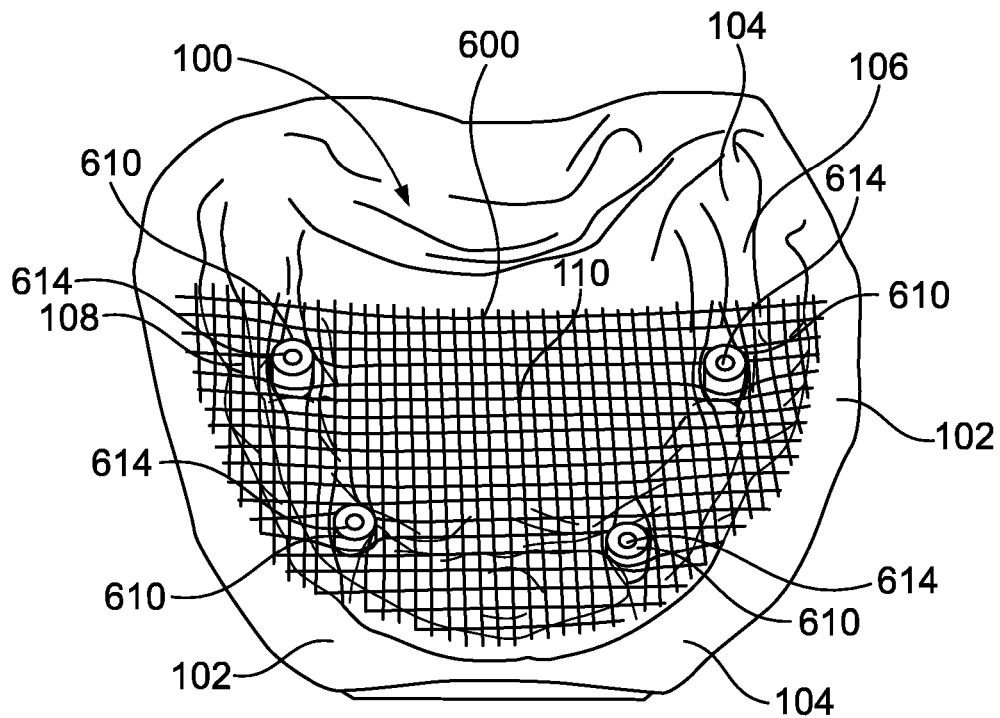
FIG. 6A is a top view of the arch area in FIG. 1A with healing abutments and pins that anchor a mesh grid.
Figure 6B:
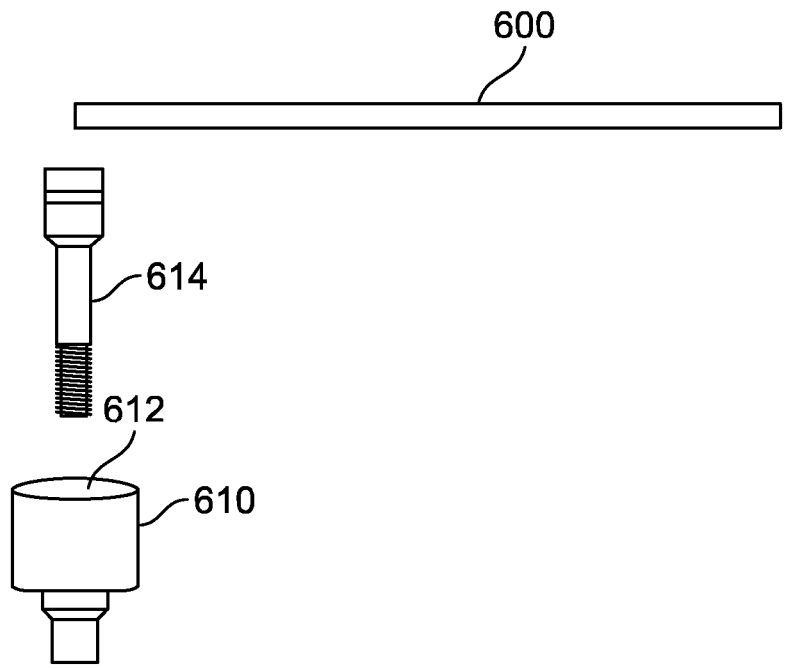
FIG. 6B is a close-up perspective view of one of the healing abutments and pins in FIG. 6A.

When installed in the arch 102, the healing abutments 500 in FIG. 5A may be used to affix other types of connecting-geometry tools to overlay the connecting geometry area 110. For example, FIG. 6A shows a mesh 600 similar to the mesh 300 in FIG. 3A which overlays the connecting area 110 in FIG. 1A. In this example, inserts (not shown) have been inserted in the arch 102. Healing abutments 610 have been connected to the inserts embedded in the arch 102 in FIG. 6A in this example. Each of the healing abutments 610 has a socket 612 for the attachment of the abutment 610 to other devices during the restoration process. In this example, specialized pins 614 have been inserted in the respective sockets 612 of the healing abutments 610 as shown in FIG. 6B. The pins 614 are in turn attached to the mesh 600 to hold the mesh 600 in place over the connecting area 110 during the scanning process. Of course, other attachment members that are connected to the imbedded inserts in the arch 102 may be used in place of the healing abutments 610 to hold the mesh 600 in place.

Figure 7:
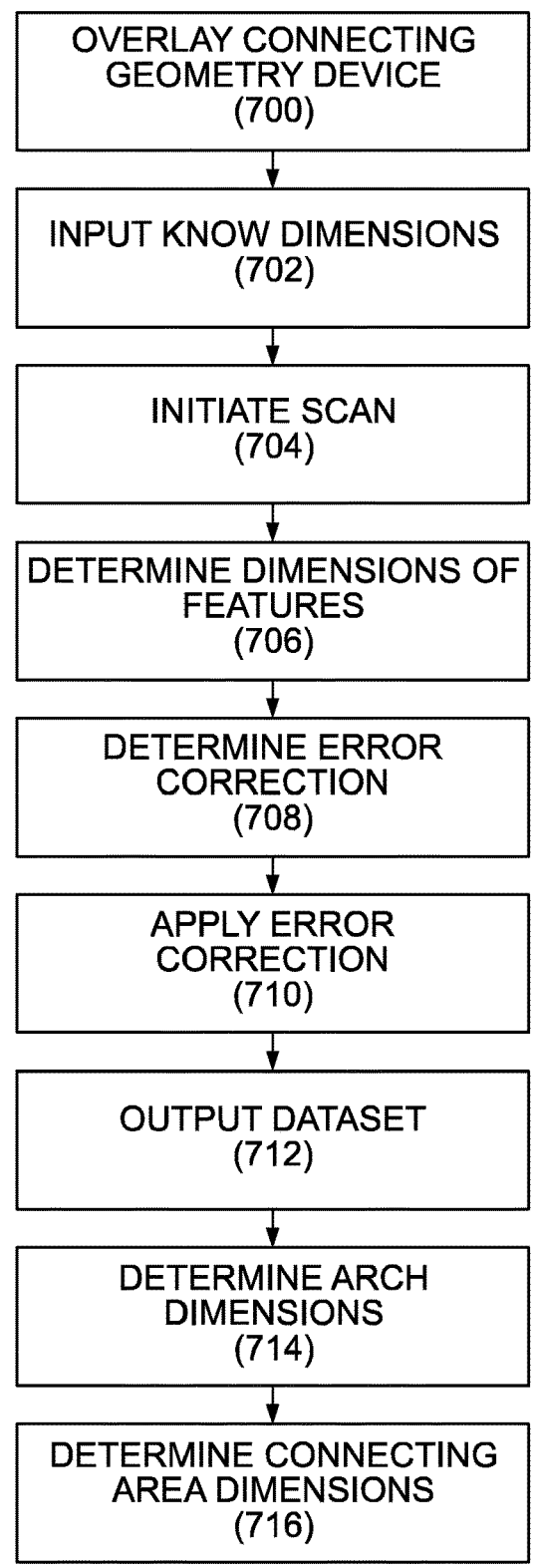
FIG. 7 is a flow diagram of the scanning process of the arch area in FIG. 1A performed with real-time error correction.

The operation of the example scan process, which may be run on a controller, will now be described with reference to FIGS. 1 and 3-6 in conjunction with the flow diagram shown in FIG. 7. The flow diagram in FIG. 7 is representative of exemplary machine readable instructions for implementing an accurate intra-oral scan. In this example, the machine readable instructions comprise an algorithm for execution by: (a) a processor, (b) a controller, and/or (c) one or more other suitable processing device(s). The algorithm may be embodied in software stored on tangible media such as, for example, a flash memory, a CD-ROM, a floppy disk, a hard drive, a digital video (versatile) disk (DVD), or other memory devices, but persons of ordinary skill in the art will readily appreciate that the entire algorithm and/or parts thereof could alternatively be executed by a device other than a processor and/or embodied in firmware or dedicated hardware in a well-known manner (e.g., it may be implemented by an application specific integrated circuit (ASIC), a programmable logic device (PLD), a field programmable logic device (FPLD), a field programmable gate array (FPGA), discrete logic, etc.). For example, any or all of the components of the process could be implemented by software, hardware, and/or firmware. Also, some or all of the machine readable instructions represented by the flowchart of FIG. 7 may be implemented manually. Further, although the example algorithm is described with reference to the flowchart illustrated in FIG. 7, persons of ordinary skill in the art will readily appreciate that many other methods of implementing the example machine readable instructions may alternatively be used. For example, the order of execution of the blocks may be changed, and/or some of the blocks described may be changed, eliminated, or combined.

FIG. 7 is a flow diagram of a process to provide an accurate scan of the arch area 100 in FIG. 1A for restoration purposes. Initially, a connecting-geometry tool such as the mesh 300 in FIG. 3A, the mesh 350 in FIG. 3B, the mesh 400 in FIG. 4, or the scan plates 502 in FIGS. 5A-5C, is affixed relative to the arch 102 to overlay at least part of the connecting geometry area 110 in FIG. 1A (700). As explained above, the connecting-geometry tool has definable features which may be registered by the scanner. The dimensions of known features of the connecting-geometry tool are then input in a scanner controller (702). These dimensions may also be previously stored in a library for the specific connecting-geometry tool for convenient access by the scanner controller. For example, if objects such as the objects 412, 414, 416 and 418 in FIG. 4 are overlaying the connecting geometry area 110, the dimensions of the objects are stored in memory for error correction purposes.

A scan is initiated of the arch area 100 and the connecting geometry area 110 to include at least part of the connecting-geometry tool for each scan frame (704). A handheld IOS device is preferably used to capture images of the areas of interest to produce the scanned dataset. Data relating to the features of the connecting-geometry tool on the connecting area is determined based on the dataset from the scan (706). The dimensions of the captured objects are compared with the recorded inputs of the known dimensions to determine error correction information (708). The error correction information (708) is incorporated into data inputs from the scan to produce a corrected scan dataset (710). A complete dataset of the arch area and connecting geometry is then output for further processing such as for determining dimensions of the arch area 100 for purposes of model construction (712). A determination of the dimensions of features of the arch 102 such as edentulous areas and teeth 104 may be determined from the corrected scan dataset (714). The dimensions of the connecting area 110 may be determined based on the data relating to the features of the connecting-geometry tool from the corrected dataset (716).

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A method of providing a three-dimensional scan of a dental arch area in a patient, the dental arch area having two segments and a homogeneous connecting area between the two segments, the method comprising:
    affixing a connecting-geometry tool with a plurality of definable features relative to the dental arch area in the patient, the plurality of definable features including a plurality of geometric shapes overlaying at least part of the homogenous connecting area;
    scanning the dental arch area to produce a scanned dataset of the arch area;
    determining data relating to the definable features of the connecting-geometry tool overlaying the connecting area based on the scanned dataset, the data including a scan interpretation dimension of the definable features;
    performing an error assessment to determine a skew in the scanned dataset in relation to a known dimension of the definable features and the scan interpretation dimension of the definable features determined from the data relating to the definable features; and
    determining, based on the skew, the dimensions of the homogenous connecting area based on the data relating to the definable features, wherein the homogenous connecting area is a cross-arch connecting area of soft tissue that separates the two segments of the dental arch.

2. The method of claim 1, further comprising correcting the scan dataset based on the error assessment to produce a corrected intra-oral scan dataset.

3. The method of claim 2, wherein the error correction is performed in real-time.

4. The method of claim 1, wherein the arch area includes at least one abutment fixed in the arch area and wherein the connecting-geometry tool is attached to the abutment and extends over the connecting area.

5. The method of claim 4, wherein the connecting-geometry tool is a plate.

6. The method of claim 5, wherein the plate includes an object of a predetermined dimension.

7. The method of claim 1, where the connecting-geometry tool extends from a first segment of the two segments of the dental arch area, across the homogenous connecting area, and to a second segment of the two segments of the dental arch area.

8. The method of claim 1, wherein the connecting-geometry tool is a mesh grid including a grid structure and each grid structure having dimensions and a shape, wherein the mesh grid includes the plurality of definable features, the plurality of definable features including the plurality of geometric shape having at least one of: a dimension different from the dimensions of each grid structure and a shape different from the shape of the grid structure.

9. The method of claim 1, wherein the dental arch area includes a first implant embedded in the dental arch area, and wherein affixing the connecting-geometry tool to the dental arch area in the patient includes coupling the connecting-geometry tool to a first implant embedded in the dental arch area, wherein the plurality of geometric shapes are transverse to a central axis of the first implant, the plurality of geometric shapes overlaying at least part of the homogenous connecting area.

10. The method of claim 9, wherein the dental arch area includes a second implant embedded in the arch area, the method further includes:
    coupling a second connecting-geometry tool with at least one definable feature to the second implant, the at least one definable feature being transverse to a central axis of the second implant, the at least one definable feature overlaying at least part of the connecting area, wherein the first and second connecting-geometry tools are attached so the definable features extend from one of the two segments of the arch area; and
    determining data relating to the definable feature of the second connecting-geometry tool overlaying the connecting area based on the scanned dataset.

11. A system for providing a three-dimensional scan of a dental arch area in a patient, the dental arch area having two segments and a homogeneous connecting area between the two segments, the system comprising:
    a connecting-geometry tool affixable to the dental arch area in the patient to overlay the homogenous connecting area, wherein the connecting-geometry tool includes a plurality of definable features having a plurality of geometric shapes overlaying at least part of the homogenous connecting area;
    an intra-oral scanner to scan the dental arch area to produce a scanned data of the dental arch area;
    a controller coupled to the intra-oral scanner, the controller is operative to:
    accept the scanned data from the intra-oral scanner;
    determine data relating to the definable features of the connecting-geometry tool overlaying the connecting area based on the scanned data, the scanned data including a scan interpretation dimension of the definable features;
    perform an error assessment to determine a skew in the scanned data in relation to a known dimension of the definable features and the scan interpretation dimension of the definable features determined from the data relating to the definable features; and
    determine, based on the skew, dimensions of the homogenous connecting area based on the data relating to the definable features, wherein the homogenous connecting area is a cross-arch connecting area of soft tissue that separates the two segments of the dental arch.

12. The system of claim 11, wherein the controller corrects the scanned data based on the error assessment to produce a corrected intra-oral scan dataset.

13. The system of claim 12, wherein the error assessment is performed in real-time.

14. The system of claim 11, wherein the connecting-geometry tool extends from a first segment of the two segments of the dental arch area, across the homogenous connecting area, and to a second segment of the two segments of the dental arch area.

15. The system of claim 11, wherein the connecting-geometry tool is a mesh grid including a grid structure and each grid structure having dimensions and a shape, wherein the mesh grid includes the plurality of definable features, the plurality of definable features including the plurality of geometric shape having at least one of: a dimension different from the dimensions of each grid structure and a shape different from the shape of the grid structure.

16. The system of claim 11, wherein the connecting-geometry tool is a plate.

* * * * *